United States Patent [19]

Fruchey

[11] Patent Number: 4,933,496

[45] Date of Patent: Jun. 12, 1990

[54] PROCESS FOR PRODUCING AN AQUEOUS 4-HYDROXYACETOPHENONE (4-HAP) WHICH IS STABLE AT ROOM TEMPERATURE

[75] Inventor: Olan S. Fruchey, Corpus Christi, Tex.

[73] Assignee: Hoechst Celanese Corporation, Somerville, N.J.

[21] Appl. No.: 348,126

[22] Filed: May 3, 1989

Related U.S. Application Data

[63] Continuation of Ser. No. 149,314, Jan. 28, 1988, abandoned.

[51] Int. Cl.$^5$ .................... C07C 103/38; C07C 49/78; C07C 131/00
[52] U.S. Cl. .................................... 568/337; 564/223; 564/300; 252/182.31
[58] Field of Search ................ 564/223, 300; 568/337; 252/182.31

[56] References Cited

U.S. PATENT DOCUMENTS 4,524,217  6/1985  Davenport et al. ................ 564/223
4,560,789  12/1985  Davenport et al. ................ 564/223
4,568,763  2/1986  Davenport et al. ................ 564/223

Primary Examiner—Carolyn S. Elmore
Attorney, Agent, or Firm—Donald R. Cassady; George A. Depaoli

[57] ABSTRACT

A process for preparing a stable 4-hydroxyacetophenone oil by mixing 4-hydroxyacetophenone with an aqueous hydroxylamine salt in the absence of added caustic, at a temperature of 50°–100° C., for about 10–60 minutes and then cooling the same is disclosed.

4 Claims, No Drawings

PROCESS FOR PRODUCING AN AQUEOUS 4-HYDROXYACETOPHENONE (4-HAP) WHICH IS STABLE AT ROOM TEMPERATURE

This application is a continuation of application Ser. No. 149,314, filed Jan. 28, 1988, now abandoned.

FIELD OF THE INVENTION

This invention relates to the production of a novel aqueous 4-hydroxyacetophenone (4-HAP) oil which is stable at room temperature. This invention eliminates the solid handling of 4-HAP during 4-hydroxyacetophenone oxime production which is used in the subsequent manufacture of N-acetyl-para-aminophenol (APAP).

BACKGROUND OF THE INVENTION

N-acetyl-para-aminophenol (APAP) is a well-known analgesic which has enjoyed tremendous commercial success. There are various processes for manufacturing the same, including acylating para-aminophenol with an acetylating agent such as acetic anhydride.

Recently, a novel process for the production of APAP has been discovered and it is the subject matter of U.S. Pat. No. 4,524,217.

The above patent discloses the production of APAP by reacting 4-hydroxyacetophenone (4-HAP) with a hydroxylamine salt and excess base to form the ketoxime of the ketone and subjecting the ketoxime to a Beckmann rearrangement in the presence of a catalyst to form the N-acyl-para-aminophenol (APAP).

As can well be appreciated, in a multi-step process such as that disclosed in U.S. Pat. No. 4,524,217, the entire disclosure of which is incorporated herein by reference, the rate and/or manner at which one intermediate is produced is not necessarily the same as for another.

Thus, in a proposed manufacturing operation for APAP, a continuous process is used for the manufacture of 4-hydroxyacetophenone whereas a batch process is used for the manufacture of the oxime from 4-HAP and the APAP from the oxime. Consequently, there is a delay time between the production of 4-HAP and its subsequent utilization to produce the oxime and the final product. A very convenient way of handling this situation is to provide a surge system which basically consists of a holding tank or tanks between the 4-HAP and the oxime/APAP production.

Although it is very possible to hold 4-HAP in a separate vessel, nevertheless there are problems which are associated with such a procedure.

It has been found that 4-HAP is thermally unstable at elevated temperatures and tends to degrade when held in a molten condition for prolonged periods of time. On the other hand, when molten 4-HAP is mixed with water at 60° C. and a 4-HAP/water/oil is formed, this material solidifies at about 45° C. Thus, in order to hold 4-HAP until it can be used, a problem has arisen in that lower temperatures result in solidification and higher temperatures cause thermal degradation. 4-HAP can be recovered as a solid but this also causes problems, namely, the problems involved in the solid handling of 4-HAP as well as the additional cost which is required to recover 4-HAP as a solid.

SUMMARY OF THE INVENTION

In accordance with this invention, N-acetyl-paraaminophenol (APAP) is produced by reacting a 4-hydroxyacetophenone (4-HAP) with a hydroxylamine salt, such as hydroxylammonium sulfate, and a base to form the ketoxime and subjecting the ketoxime to a Beckmann rearrangement to produce APAP.

The improvement with which this invention is concerned resides in the fact that it has been found that if 4-HAP is treated with hydroxylammonium sulfate (HAS) at a temperature of 50°-100° C. and then held for about 5-15 minutes, a novel aqueous 4-HAP oil is formed which does not solidify upon cooling to room temperature. By forming the stable oil of this invention, 4-HAP can be held at low temperatures which will not create problems, such as color problems and stability problems. When it is desired to produce the oxime which can then be subjected to the Beckmann rearrangement, the 4-HAP oil can be fed to a ketoxime reactor which contains make-up water, then caustic is added in order to produce oxime in the conventional manner.

As has been previously pointed out, the novel 4-HAP oil of this invention can be generated by mixing molten 4-HAP with a commercially available aqueous solution of hydroxylammonium sulfate (HAS). The commercially available solution is 30% by weight of HAS.

As is known, in order to form a ketoxime by reacting the hydroxyamine sulfate with the corresponding ketone, it is necessary to add base. In the novel process of this invention, base is not added in forming the novel 4-HAP oil for the reason that complete conversion to the oxime is not desired. Thus, as has been previously pointed out, the novel 4-HAP oil of this invention can be generated by mixing 4-HAP with a 30% HAS solution at temperatures ranging from 50°-100° C. and preferably from 80°-95° C. and particularly preferred from 80°-85° C. Too low a temperature results in some solid formation which dissolves with time. Too high a temperature, within reasonable limits, does not gain anything and results in a waste of energy.

It is necessary that the 4-HAP and HAS solution be mixed in order to prevent premature phase separation and acceptable mixing times usually range in the order of from about 10 to about 60 minutes.

Following mixing, the 4-HAP/HAS solution should be cooled to around room temperature, i.e., 20° C., so that phase separation can take place. It is interesting to note that the phase separation should take place at a temperature which is lower than the storage temperature in order to prevent further phasing during storage. Phase separation generally takes place in about 5-10 minutes at 20° C. but both phases are cloudy. It has been found that the phases clear within about 60 minutes. Therefore, the residence time in the phase tank, at about 20° C., should be about 60 minutes. The organic phase will be the bottom phase in the decanter.

The following table represents the average of three runs on the organic phase of the novel composition of this invention.

TABLE

| | |
|---|---|
| 4-HAP | 28.5% (24.7-32.9%) |
| 4-HAP Oxime | 28.5% (16.9-36.5%) |
| Water | 27.4% (27.1-27.7%) |
| HAS | 15.3% (2.7-31.1%) |
| Balance, including APAP | Less than 0.3% |

TABLE-continued and others

From the above table, it can be seen that the novel composition of this invention fluctuates depending upon the conversion of the 4-HAP to 4-HAP oxime. As the 4-HAP oxime increases in the novel composition of this invention, the HAS decreases. The following examples will illustrate the best mode now contemplated by the inventor for carrying out this invention.

EXAMPLE 1

HAS solids (63.6 grams) were dissolved in 150 ml water and warmed to 80° C. The HAS solution was placed in an 80° C. water bath and 100 g of molten 4-HAP was added quickly and the solution was stirred for 15 minutes and then cooled to 20° C. in an ice bath while stirring. The stirring was stopped and the phases were separated and weighed. The two phases were stored in a sealed bottle for 7 days and good stability was observed.

EXAMPLE 2

The procedure of Example 1 was repeated with the sole exception that after the molten 4-HAP was added, the solution was stirred for 60 minutes as opposed to 15 minutes. All other steps were identical. After 7 days, excellent stability was observed.

EXAMPLE 3

HAS solids (63.9 grams) were dissolved in 430 ml of water and warmed to 80° C. The HAS solution was placed in an 80° C. water bath and 100 grams of molten 4-HAP was quickly added. The solution was stirred for 15 minutes then cooled to 20° C. in an ice bath with stirring. The stirring was stopped and phase separation took place, and the two phases were stored in sealed bottles for 7 days. However, significant solids formation within 24 hours resulted making this approach impractical. As can be seen, the concentration of HAS in this example was 13%.

EXAMPLE 4

The procedure of Example 3 was repeated with the sole exception that after the molten 4-HAP was quickly added, the solution was stirred for 60 minutes as opposed to 15 minutes as in Example 3. The two phases were stored in a sealed bottle for 7 days. Precipitation was found to occur, thereby rendering this procedure impractical. It is noted that this example also utilized 13% HAS as opposed to 30%.

The following Table illustrates the results obtained in Examples 1–4. It is noted that for Examples 1 and 2 the samples were repeated in triplicate.

TABLE 1

| Example | Sample # | Organic/ Aqueous Phase | Residence Time | Phase Analyses | | | | | | | Wt. (g) of Phase |
|---|---|---|---|---|---|---|---|---|---|---|---|
| | | | | [HAS] | 4-HAP | Oxime | APAP | HAS* | H$_2$O | Others | |
| 1 (a) | 35333-23-1 | Organic | 15 min | 30% | 27.75 | 32.30 | .22 | 12.2 | 27.5 | .0016 | 152.1 |
| 1 (b) | 35333-23-2 | Aqueous | 15 min | 30% | 1.50 | 3.12 | .017 | 24.5 | 70.9 | ND | 126.6 |
| 1 (c) | 35333-28-1 | Organic | 15 min | 30% | 24.67 | 16.92 | .164 | 31.1 | 27.1 | .003 | 152.9 |
| 1 (d) | 35333-28-2 | Aqueous | 15 min | 30% | 1.17 | 3.27 | .014 | 25.7 | 69.8 | ND | 117.3 |
| 1 (e) | 35333-29-1 | Organic | 15 min | 30% | 32.93 | 36.48 | .16 | 2.7 | 27.7 | ND | 152.4 |
| 1 (f) | 35333-29-2 | Aqueous | 15 min | 30% | 2.64 | 1.91 | .015 | 29.2 | 71.2 | .001 | 125.6 |
| 2 (a) | 35333-24-1 | Organic | 60 min | 30% | 29.05 | 39.62 | .017 | 2.7 | 27.7 | .0023 | 150.2 |
| 2 (b) | 35333-24-2 | Aqueous | 60 min | 30% | 1.07 | 2.53 | .94 | 32.4 | 63.9 | ND | 85.2 |
| 2 (c) | 35333-30-1 | Organic | 60 min | 30% | 31.72 | 35.06 | 1.31 | 3.4 | 28.5 | .057 | 147.5 |
| 2 (d) | 35333-30-2 | Aqueous | 60 min | 30% | 2.34 | 1.56 | .082 | 23.6 | 72.4 | .001 | 140.1 |
| 2 (e) | 35333-31-1 | Organic | 60 min | 30% | 40.69 | 23.98 | 1.23 | 6.2 | 27.9 | .023 | 161.4 |
| 2 (f) | 35333-31-2 | Aqueous | 60 min | 30% | 2.28 | 1.40 | .071 | 24.3 | 72.0 | .001 | 129.2 |
| 3 (a) | 35333-25-1 | Organic | 15 min | 13% | 39.06 | 31.56 | .07 | .1 | 29.1 | ND | 118.3 |
| 3 (b) | 35333-25-2 | Aqueous | 15 min | 13% | 2.74 | 3.14 | .01 | 10.3 | 83.8 | ND | 412.7 |
| 4 (a) | 35333-26-1 | Organic | 60 min | 13% | 39.02 | 32.84 | .38 | 0 | 29.8 | .0021 | 128.0 |
| 4 (b) | 35333-26-2 | Aqueous | 60 min | 13% | 2.78 | 3.29 | .048 | 12.0 | 81.9 | ND | 332.7 |

*The HAS numbers were obtained by difference and may not reflect the true level of HAS in either the organic or aqueous phase.

As pointed out in Table 1, the procedure of Examples 1 and 2 yielded stable emulsion which could be stored for a period of at least 7 days whereas the procedure of Examples 3 and 4 yielded unacceptable emulsion. Please note that the compositions of Example 3 and Example 4 are outside the composition being claimed.

EXAMPLE 5

In order to demonstrate that the novel 4-HAP emulsion can be used to produce the corresponding ketoxime, the following procedure was carried out. The organic and aqueous phases from both Examples 1(a) and 1(b) and 2(a) and 2(b) were placed in a 1 liter round-bottom flask along with 230 ml of water. The flask was equipped with a reflux condenser and an additional funnel which contained 40 ml of 50% by weight sodium hydroxide solution and 50 ml of water. The contents were heated to reflux and the caustic added dropwise over a 10-minute period, after which the solution was allowed to reflux for 30 minutes and then cooled to room temperature. The white solids were filtered, washed with 100 ml of water, and then dried at 60° C. for 1 hour.

The above procedure was carried out twice. In the first experiment, Example 1(a) and Example 1(b) were combined and, in the second, Example 2(a) and Example 2(b) were combined. The oxime was produced in both cases.

What is claimed is:

1. A process for the preparation of a stable aqueous 4-hydroxyacetophenone oil which comprises mixing molten 4-hydroxyacetophenone with a 30% aqueous solution of hydroxylamine salt in the absence of added caustic at a temperature of 50°–100° C. for about 10 to 60 minutes and cooling the same in order to form a stable oil.

2. The process of claim 1 wherein said hydroxylamine salt is hydroxylammonium sulfate.

3. The process of claim 2 wherein said temperature is 80°–95° C.

4. The process of claim 3 wherein said temperature is 80°–85° C.

* * * * *